(12) United States Patent
Maack

(10) Patent No.: US 10,918,352 B2
(45) Date of Patent: Feb. 16, 2021

(54) DEVICE AND METHOD FOR SCATTER CORRECTION IN AN X-RAY IMAGE

(71) Applicant: KONINKLIJKE PHILIPS N.V., Eindhoven (NL)

(72) Inventor: Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/342,696

(22) PCT Filed: Jul. 9, 2018

(86) PCT No.: PCT/EP2018/068490
§ 371 (c)(1),
(2) Date: Apr. 17, 2019

(87) PCT Pub. No.: WO2019/011832
PCT Pub. Date: Jan. 17, 2019

(65) Prior Publication Data
US 2020/0229785 A1 Jul. 23, 2020

(30) Foreign Application Priority Data

Jul. 13, 2017 (EP) .................................... 17181182

(51) Int. Cl.
*A61B 6/00* (2006.01)
*G06T 5/00* (2006.01)
*G06T 5/50* (2006.01)

(52) U.S. Cl.
CPC .......... *A61B 6/5282* (2013.01); *A61B 6/4035* (2013.01); *A61B 6/4291* (2013.01);
(Continued)

(58) Field of Classification Search
None
See application file for complete search history.

(56) References Cited

U.S. PATENT DOCUMENTS 9,519,068 B2   12/2016  Gibson
9,804,106 B2 *  10/2017  Rothe ..................... G21K 1/02
(Continued)

FOREIGN PATENT DOCUMENTS

DE   102016206559 B3   6/2017
EP       2196148 A1    6/2010
(Continued)

*Primary Examiner* — Thomas R Artman
(74) *Attorney, Agent, or Firm* — Larry Liberchuk

(57) ABSTRACT

The present invention relates to a device for scatter correction in an X-ray image, the X-ray image (30, 40) having a superimposed structured pattern, the device (1) comprising: an X-ray image receiving element (10); a pattern remover (11); and a first subtraction module (12); wherein the X-ray image receiving element (10) is configured to receive an X-ray image (30, 40) comprising a superimposed structured pattern (31); wherein the pattern remover (11) is configured to remove the structured pattern (31) from the X-ray image (30, 40) resulting in a pattern corrected X-ray image (43); wherein the first subtraction module (12) is configured to subtract the pattern corrected X-ray image (33, 43) from the X-ray image (40) resulting in a structured pattern image (32, 42); and wherein a contrast measurement unit (13) is configured to apply a local structure contrast measurement function to the structured pattern image (32, 42) resulting in a structure contrast image (34, 44). The invention improves the scatter correction of an X-ray image.

13 Claims, 7 Drawing Sheets

(52) U.S. Cl.
CPC .............. *A61B 6/484* (2013.01); *G06T 5/002* (2013.01); *G06T 5/50* (2013.01); *G06T 2207/10116* (2013.01)

(56) References Cited

U.S. PATENT DOCUMENTS

| | | | |
|---|---|---|---|
| 2003/0016854 A1 | 1/2003 | Inoue | |
| 2003/0091243 A1 | 5/2003 | Sasada | |
| 2009/0316857 A1 | 12/2009 | David | |
| 2010/0046822 A1 | 2/2010 | Li | |
| 2010/0074395 A1 | 3/2010 | Popescu | |
| 2010/0104165 A1 | 4/2010 | Takahashi | |
| 2011/0085639 A1 | 4/2011 | Nakamura | |
| 2012/0134472 A1 | 5/2012 | Kaneko | |
| 2012/0145912 A1* | 6/2012 | Iwakiri | A61B 6/06 250/370.08 |
| 2012/0163554 A1* | 6/2012 | Tada | A61B 6/4291 378/154 |
| 2013/0148786 A1 | 6/2013 | Kruschel | |
| 2013/0170618 A1 | 7/2013 | Koehler | |
| 2015/0342554 A1 | 12/2015 | Detlef | |
| 2015/0379711 A1 | 12/2015 | Imai | |
| 2016/0235384 A1 | 8/2016 | Enomoto | |
| 2016/0258885 A1* | 9/2016 | Rothe | G01N 23/046 |
| 2016/0296191 A1 | 10/2016 | Silver | |
| 2017/0161882 A1 | 6/2017 | Mantiuk | |
| 2020/0022668 A1* | 1/2020 | Maack | A61B 6/50 |

FOREIGN PATENT DOCUMENTS

| | | |
|---|---|---|
| GB | 2498615 A | 7/2013 |
| GB | 2521409 A | 6/2015 |
| GB | 2532634 A | 5/2016 |
| GB | 2532897 A | 6/2016 |
| GB | 2533233 A | 6/2016 |
| WO | WO2012056992 A1 | 5/2012 |
| WO | WO2012057045 A1 | 5/2012 |
| WO | WO2019020748 A1 | 1/2019 |

* cited by examiner

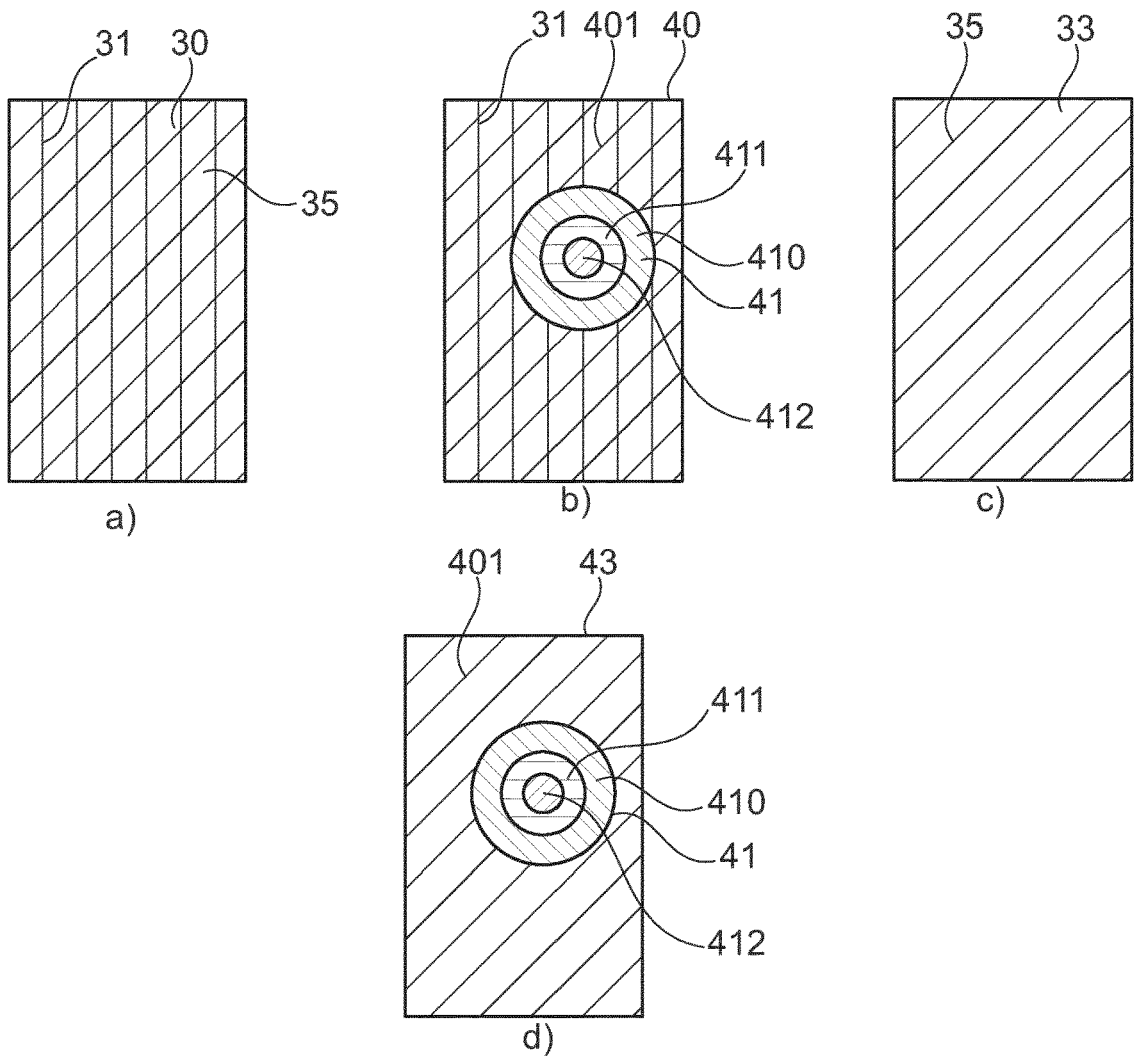
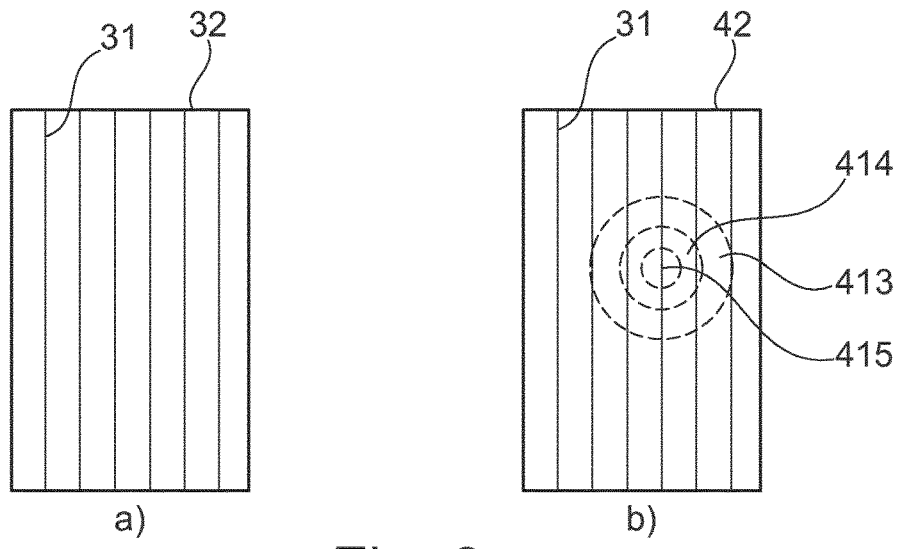
Fig. 6

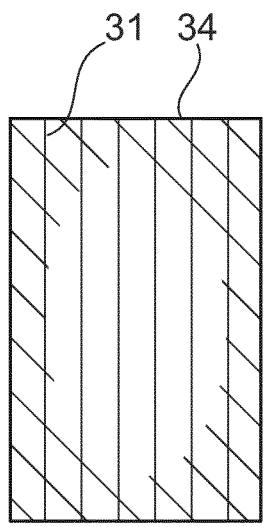 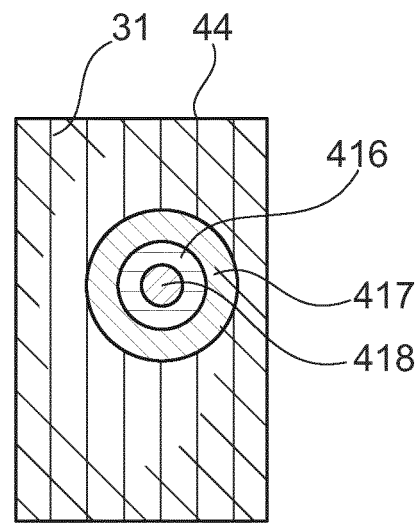
Fig. 7
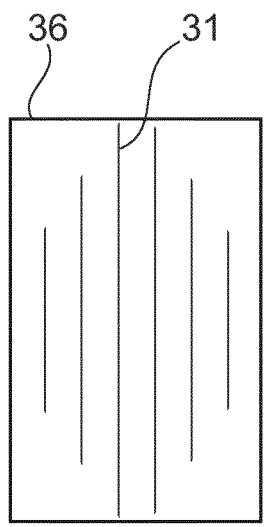 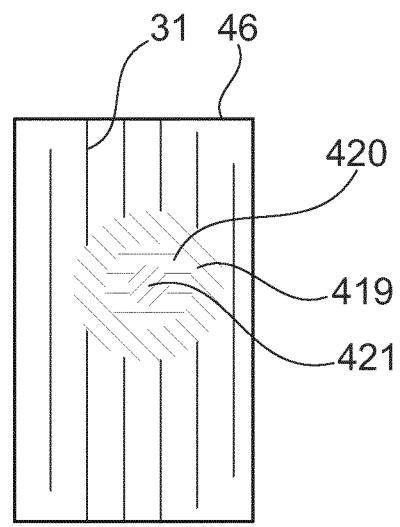
Fig. 8

DEVICE AND METHOD FOR SCATTER CORRECTION IN AN X-RAY IMAGE

FIELD OF THE INVENTION

The present invention relates to a device for scatter correction in an X-ray image having a superimposed structured pattern and a method for scatter correction in an X-ray image having a superimposed structured pattern.

BACKGROUND OF THE INVENTION

X-ray images provide insight into the internal structures of a body. For example, the bone structure can be examined in X-ray images of a body. During the X-ray image acquisition process the X-ray radiation in the acquisition device is scattered such that the X-ray image being produced may become blurred.

The scattered radiation may be reduced by using a grid in the acquisition device. It is known to remove the structures which are generated by the grid in the X-ray image with pattern removal processes.

For example, EP 2 196 148 A1 uses a grid for reducing the scattering radiation. A radiological image processing apparatus comprises a separating device using frequency analysis and a bandpass filter processing for separating the radiological image into a grid image including the components of a grid figure and a non-grid image including other components. Furthermore, a removing device subtracts an intensity adjusted non-grid image from the non-grid image to generate a corrected image free of the influence of the grid. However, the processed X-ray image still comprises scatter structures.

Further, US 2003/0091243 A1 provides a method and apparatus for periodical pattern suppression in an image signal. A spatial frequency component corresponding to a periodical pattern included in an image signal is extracted from the image signal by subjecting the image signal to a one-dimensional filtering process in the same direction as that of the periodical pattern and in the direction perpendicular to that of a grid image. By subtracting the extracted spatial frequency component from the image signal the spatial frequency component occurring in the image signal is suppressed.

SUMMARY OF THE INVENTION

There may thus be a need to provide a device and a method which further improves the scatter correction of an X-ray image.

The object of the present invention is solved by the subject-matter of the independent claims; further embodiments are incorporated in the dependent claims. It should be noted that the following described aspects of the invention apply also for the inventive system.

According to the present invention, a device for scatter correction in an X-ray image, the X-ray image having a superimposed structured pattern, comprises: an X-ray image receiving element; a pattern remover; and a first subtraction module; wherein the X-ray image receiving element is configured to receive an X-ray image comprising a superimposed structured pattern; wherein the pattern remover is configured to remove the structured pattern from the X-ray image resulting in a pattern corrected X-ray image; and wherein the first subtraction module is configured to subtract the pattern corrected X-ray image from the X-ray image resulting in a structured pattern image.

The pattern corrected X-ray image shows the X-ray image without the structured pattern. If the X-ray image comprises an object, the pattern corrected X-ray image shows the object. If the X-ray image does not comprise an object, the pattern corrected X-ray image shows a pattern corrected reference image, i.e. a flat pattern corrected image.

The invention is used to improve the contrast of X-ray images comprising a superimposed structured pattern resulting from a grid which is used for reducing the scatter of the X-ray image acquisition system. Therein, a grid reduces the scatter from the X-ray acquisition device during the X-ray image acquisition. However, the grid superimposes a pattern structure on the X-ray image and does not remove all the scatter in the image.

The pattern structure is removed by the pattern remover. For reducing the scatter in the corrected X-ray image further, the pattern structure itself is isolated in a structured pattern image. The isolated pattern structure in the structured pattern image may then be used to further reduce the scatter in the pattern corrected X-ray image. By analyzing the structured pattern image the remaining scatter in the image may be determined. Thus, with the help of the structured pattern image the scatter resulting from the grid line contrast may be quantified. After the determination of the scatter resulting from the structured pattern, the corrected X-ray image may be processed using the determined scatter from the structured pattern image. After that processing, the scatter resulting from the grid will be reduced in the corrected X-ray image. Therefore, the contrast of the further processed corrected X-ray image will be improved.

In an example, the device may comprise a processing unit wherein the processing unit controls the components of the device.

In an example, the pattern remover may use a gridline removal software.

If the structured pattern is not only introduced for the purpose to measure and correct the scattered radiation, the present invention may improve a pure software correction for X-ray images having a structured pattern.

Further, the device further comprises: a contrast measurement unit; wherein the contrast measurement unit is configured to apply a local structure contrast measurement function to the structured pattern image resulting in a structure contrast image.

In an example, the local structure contrast measurement function may comprise an absolute value function, a minimum function, a maximum function, a standard deviation function, an average function, a median function, or a local FFT function for the amplitude etc. In an embodiment of the above example, the local structure measurement function may be carried out for a local kernel environment of e.g. 1 mm^2 as average function using a kernel of 1 mm and the absolute value of the structured pattern image, as median function using a kernel of 1 mm and the absolute value of the structured pattern image, as standard deviation function within a kernel of 1 mm, as difference function providing the difference between a maximum using a kernel of 1 mm and a minimum using a kernel of 1 mm, or as amplitude function resulting from a local Fast Fourier Transformation (FFT).

In a further example, the device further comprises: a filter element; wherein the filter element is a low pass filter for the structure contrast image providing a filtered structure contrast image.

In another example, the device further comprises: an estimation unit; wherein the estimation unit is configured to estimate a primary fraction of the X-ray image, wherein the estimation is based on the filtered structure contrast image.

In an example, the estimation unit estimates the primary fraction based on the ratio between the filtered structure contrast image and a filtered reference structured pattern image wherein the reference structured pattern image is based on a reference X-ray image having a structured pattern but lacking an object. The reference X-ray image has the same focal spot position as the X-ray image.

In further example, the device comprises a linearization module which determines a linearized pattern corrected X-ray image X from X=10^PRE_Gc wherein PRE_Gc is the pattern corrected image.

In a first embodiment, a scatter corrected X-ray image P may be determined by multiplying the primary fraction with the linearized pattern corrected X-ray image.

In a second embodiment providing a scatter corrected X-ray image with reduced noise, the device is e.g. carried out as that the device further comprises: a determination module; and a second subtraction module; wherein the determination module is configured to provide a filtered scatter signal based on a scatter fraction being determined from the primary fraction or a value derived from the scatter fraction; wherein the second subtraction module is configured to subtract at least a fraction of the filtered scatter signal from the pattern corrected X-ray image resulting in a scatter corrected X-ray image.

In an example, the determination module may first determine a scatter fraction SF from the primary fraction PF using SF=1−PF. The scatter signal S may then be determined by S=X*SF, wherein X is a linearized pattern corrected X-ray image.

In an example, the second filter device may comprise a quite large filter kernel, i.e. more than 1 cm, S'=LP[S].

In a further example, the second subtraction module subtracts the scatter signal from a linearized pattern corrected X-ray image P=X−S'.

In a further example, the device comprises a logarithm unit which determines the logarithm of the scatter corrected X-ray image resulting in an output X-ray image PRE_Gc_Sc=10^P.

In a further example, for providing the filtered signal, the determination module is configured to apply a low pass filter on the scatter fraction or a value derived from the scatter fraction.

According to the present invention, also a system for scatter correction in an X-ray image having a superimposed structured pattern, comprises: An X-ray image acquisition device; and a device according to one of the preceding claims; wherein the X-ray image acquisition device comprises: a structure pattern element; wherein the X-ray image acquisition device provides an X-ray image comprising a structured pattern image component.

In an example, the X-ray image acquisition device is a dark field X-ray image acquisition device.

In an example, the structure pattern element may be a structure pattern grating arranged between a G2 grating and a detector of the X-ray image acquisition device.

In another example, a G2 grating of the X-ray image acquisition device may comprise the anti-scatter element. The anti-scatter element may then comprise super-positioned stripes with a spatial frequency close to the Nyquist frequency of the detector of the X-ray image acquisition device. The super-positioned stripes may e.g. be carried out by increasing the height of some lamellas of the G2 grid. The lamellas have then to be chosen such that the lamellas with increased height provide a structured pattern on the resulting X-ray image. For example, lamellas having a distance of 144 μm may be increased in height by 50 μm.

In another example a duty cycle of the G2 grating may be modulated. A grating with a period of 10 μm and 5 μm metal and 5 μm interspace has a duty cycle of 50%. The duty cycle may be modulated such that the G2 grating has 150 μm of a first duty cycle of 50% and 150 μm of a second duty cycle of 60% alternating, wherein the second duty cycle has 6 μm metal and 4 μm interspace. This also may provide a structure pattern on the X-ray image.

In a further example, the structure pattern element may be a plate with stripes. The plate may be arranged between the G2 grating and the detector of the detector for scatter quantification. The plate may be made of POM or PMMA and may have grooves in pixel size separation.

In a further example the structure pattern element may be an oscillating grid. The oscillation grid may comprise an orientation rotated by 90 degrees with respect to common scatter reducing grids and use them as oscillating grids. The structured patterns will be visible despite the oscillation, so the invention may reduce the scatter from the resulting X-ray image. The fixed pattern will be blurred to the oscillation, so the image be further improved. The system does not need to be modified in the way the acquisition process is performed.

In a further example, the scatter correction according to the invention is a software option in the system. The system may further comprise a grid recognition element, which is configured to identify the grid with an identificatory unit, e.g. a bar code reader. The scatter correction according to the invention may then automatically be applied to those images which comprise a superimposed structured pattern.

According to the present invention, also a method for scatter correction in an X-ray image having a superimposed structured pattern comprises the following steps: a) receiving an X-ray image having a superimposed structured pattern; and b) removing the structured patterns from the X-ray image with a pattern remover resulting in a pattern corrected X-ray image; c) subtracting the pattern corrected X-ray image from the X-ray image with a first subtraction module resulting in a structured pattern image.

Further, the method comprises the further step: d) applying a local contrast measurement function to the structured pattern image with a contrast measurement unit resulting in a structure contrast image.

In a further example, the method comprises the further step: e) estimating a primary fraction of the X-ray image based on the structure contrast pattern image with an estimation unit.

Further, in an example, the method comprises the further steps: f) determining a filtered scatter signal from the primary fraction or a value derived from the primary fraction with a determination module; g) subtracting the at least a fraction of the filtered scatter signal from the pattern corrected X-ray image with a second subtraction module resulting in a scatter corrected X-ray image.

In another example, the step f) comprises the sub-step: f1) applying a low pass filter on the primary fraction or a value derived from the primary fraction for providing the filtered signal.

According to the present invention, also a computer program element for controlling an apparatus described above, which, when being executed by a processing unit, is adapted to perform the method according to the description above.

According to the present invention, also a computer readable medium has stored the program element mentioned above.

These and other aspects of the present invention will become apparent from and be elucidated regarding the embodiments described hereinafter.

BRIEF DESCRIPTION OF THE DRAWINGS

Exemplary embodiments of the invention will be described in the following regarding the following drawings:

FIG. 5a-d show schematic drawings of a flat X-ray image (a), an X-ray image comprising an object (b), a pattern corrected flat X-ray image (c), and a pattern corrected X-ray image (d).

FIG. 6a, b show schematic drawings of a subtraction of a pattern corrected flat image from a flat X-ray image of FIG. 5a (a) and of a pattern corrected X-ray image of FIG. 5d from an X-ray image comprising an object of FIG. 5b (b).

FIG. 7a, b show schematic drawings of a structure contrast image of FIG. 6a (a) and FIG. 6b (b).

FIG. 8a, b show schematic drawings of filtered structure contrast images of FIG. 7a (a) and FIG. 7b (b).

FIG. 9 shows a schematic drawing of a primary fraction of the X-ray image comprising an object determined by the quotient of FIG. 8b and FIG. 8a.

DETAILED DESCRIPTION OF EMBODIMENTS

Figure 1:
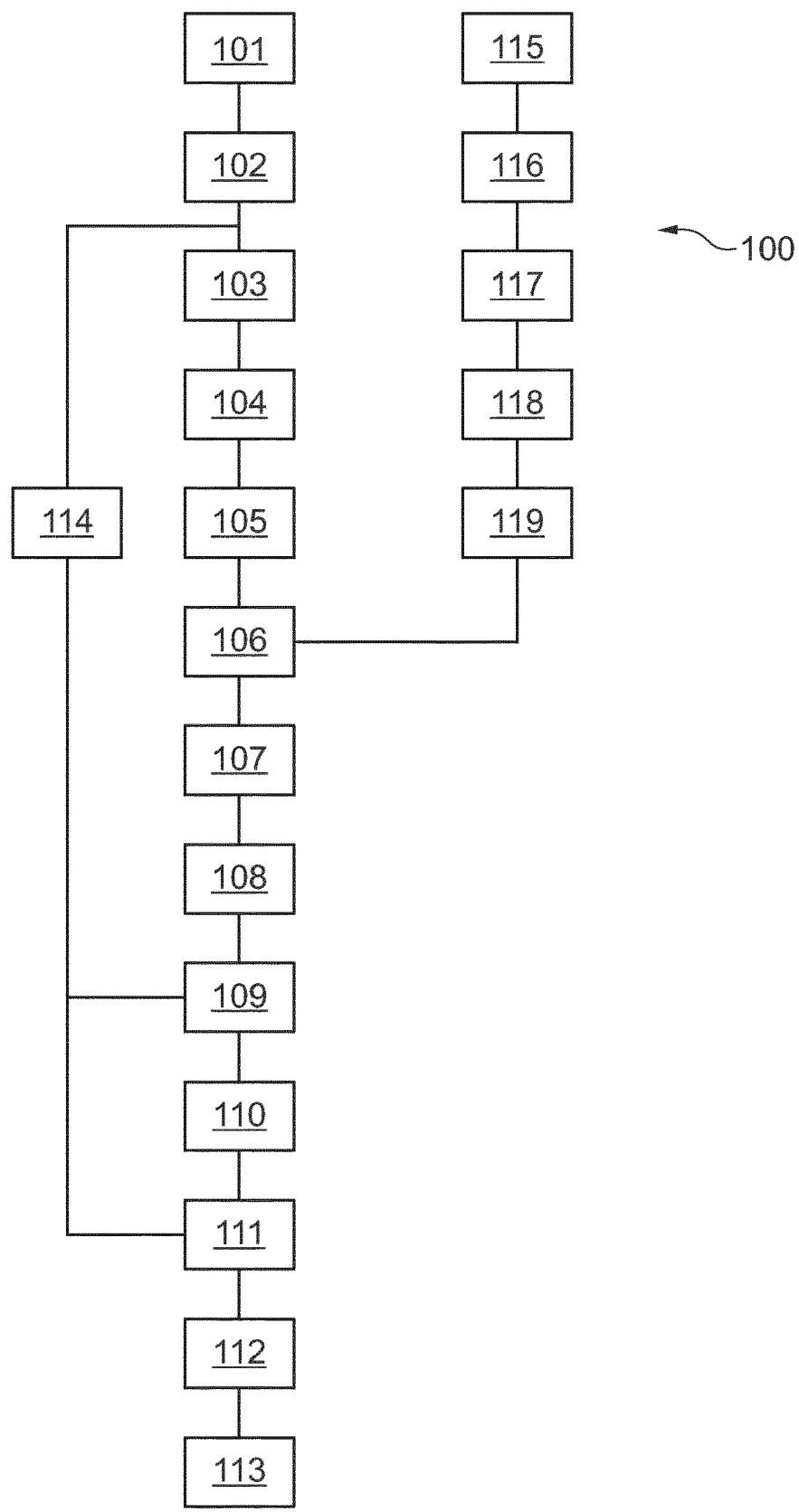
FIG. 1 shows a schematic flowchart of an embodiment of the method.

Before further describing the imaging system and the device, examples of a method are described in further detail referring to FIG. 1.

FIG. 1 shows a schematic flowchart of an embodiment of the inventive method 100. The flowchart shows two branches starting with step 101 and with step 115. The branches connect in step 106. The branch starting with step 101 has as input an X-ray image with superimposed structured patterns comprising an object whereas the branch starting with step 115 has as input a flat calibration image with a superimposed structured pattern. Examples of the input images are shown in FIGS. 5a and 5b.

In step 101 the X-ray image having a superimposed structured pattern is received. In a first embodiment, the X-ray image having a superimposed structured pattern may be image data proportional to the logarithm of a detector signal. Due to the exponential absorption, the logarithmic data is proportional to the shape and thickness of the examined object. The logarithmic image data is default output of detector systems. In a second embodiment of the X-ray image having a superimposed structured pattern may be image data being proportional to the X-ray radiation. In the second embodiment, the image data is therefore linearized logarithmic data of the first embodiment.

In step 102 the superimposed structured pattern is removed from the X-ray image having a superimposed structured pattern. The removal may be performed with an algorithm, e.g. software. The removal of the grid lines is independent whether the input data results from the first or the second embodiment. The result is a pattern corrected X-ray image. The pattern corrected X-ray image comprises some scatter which has not been removed before. An example of a pattern corrected X-ray image is shown in FIG. 5d.

Step 103 provides a subtraction of the pattern corrected X-ray image from the X-ray image having the superimposed structured pattern. The subtraction may be performed by a first subtraction module. The result is a structured pattern image. The structured pattern image comprises the superimposed structured pattern as well as some scattered object data. An example is shown in FIG. 6b.

A local structure contrast measurement function is applied to the structured pattern image in step 104. The local structure contrast measurement may be performed by a contrast measurement unit. The local structure contrast measurement function may be an absolute value function, a minimum function, a maximum function, a standard deviation function, an average function, a median function, or a local FFT function for the amplitude etc. in the described embodiments the local structure contrast measurement function is an absolute value function. Therefore, the absolute value of the structured pattern image is determined by the local structure contrast measurement function. The result is a structure contrast image. An example of a structure contrast image is shown in FIG. 7b.

In step 105 a filter is applied to the structure contrast image by a filter element. The filter element may be a low pass filter. The low pass filter may be a low pass filter with a small kernel. Therefore, high frequent fluctuations in the structure contrast image are filtered from the structure contrast image. The result is a filtered structure contrast image. The filtered structure contrast image is an image showing maximum structured pattern contrast in the absence of Compton scatter. An example of a filtered structure contrast image is shown in FIG. 8b.

In step 115 the flat calibration image with a superimposed structured pattern is received. In a first embodiment, the flat calibration image having a superimposed structured pattern may be image data proportional to the logarithm of a detector signal. The logarithmic image data is default output of detector systems. In a second embodiment of the flat calibration image having a superimposed structured pattern may be image data being proportional to the X-ray radiation. In the second embodiment, the image data is therefore linearized logarithmic data of the first embodiment.

In step 116 the superimposed structured pattern is removed from the flat calibration image having a superimposed structured pattern. The removal may be performed with an algorithm, e.g. software. The removal of the structured pattern is independent whether the input data results from the first or the second embodiment. The result is a pattern corrected flat image. The pattern corrected flat image comprises some scatter which has not been removed before. An example of a pattern corrected flat image is shown in FIG. 5c.

Step 117 provides a subtraction of the pattern corrected flat image from the flat calibration image having the superimposed structured pattern. The subtraction may be performed by a first subtraction module. The result is a flat structured pattern image. The flat structured pattern image comprises the superimposed structured pattern. An example is shown in FIG. 6a.

A local structure contrast measurement function is applied to the flat structured pattern image in step 118. The local structure contrast measurement may be performed by a contrast measurement unit. The local structure contrast measurement function may be an absolute value function, a minimum function, a maximum function, a standard deviation function, an average function, a median function, or a local FFT function for the amplitude etc. in the described embodiments the local structure contrast measurement function is an absolute value function. Therefore, the absolute value of the flat structured pattern image is determined by the local structure contrast measurement function. The result is a flat structure contrast image. An example of a flat structure contrast image is shown in FIG. 7a.

In step 119 a filter is applied to the flat structure contrast image by a filter element. The filter element may be a low pass filter. The low pass filter may be a low pass filter with a small kernel, i.e. equal to or lower than 1 mm. Therefore, high frequent fluctuations in the flat structure contrast image are filtered from the flat structure contrast image. The result is a filtered flat structure contrast image. The filtered flat structure contrast image is an image showing maximum structured pattern contrast in the absence of Compton scatter. An example of a filtered flat structure contrast image is shown in FIG. 8a.

Figure 9:
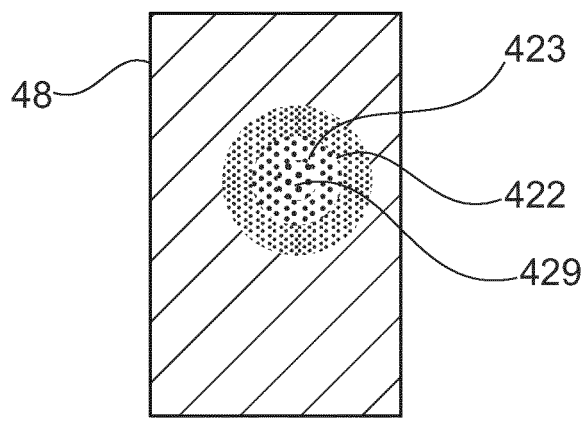
Figure 10:
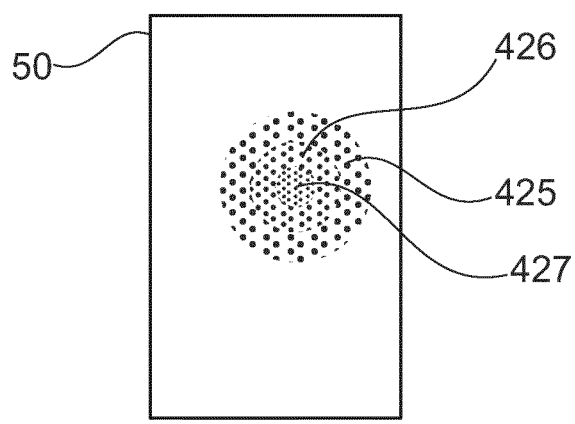
FIG. 10 shows a schematic drawing of a scatter fraction of the X-ray image comprising an object determined by the difference of FIG. 9 from 100%.

The filtered structure contrast image of step 105 and the filtered flat structure contrast image of step 119 are input of step 106 which estimates a primary fraction of the X-ray image comprising a superimposed structured pattern with an estimation unit. The estimation of the primary fraction is performed by determining the quotient of the filtered structure contrast image and the filtered flat structure contrast image. The filtered structure contrast image is divided by the filtered flat structure contrast image. An example of a primary fraction is shown in FIG. 9. The primary fraction is the quotient of the primary radiation being the X-ray radiation without any scatter and the total signal of the X-ray image with the superimposed structures. Furthermore, the primary radiation is the X-ray radiation that contributes to the visible image. Thus, the primary fraction is the fraction of the primary radiation in the total image, i.e. the linearized version of the X-ray image comprising a superimposed structured pattern. A further part of the total image is the scatter radiation. The sum of the scatter radiation and the primary radiation result in the total image. In step 107 the scatter fraction determining the fraction of the scatter radiation in the total image is determined by the primary fraction. The determination may be performed by subtracting the primary fraction from 100%, i.e. 1. An example of the scatter fraction is shown in FIG. 10.

Figure 11:
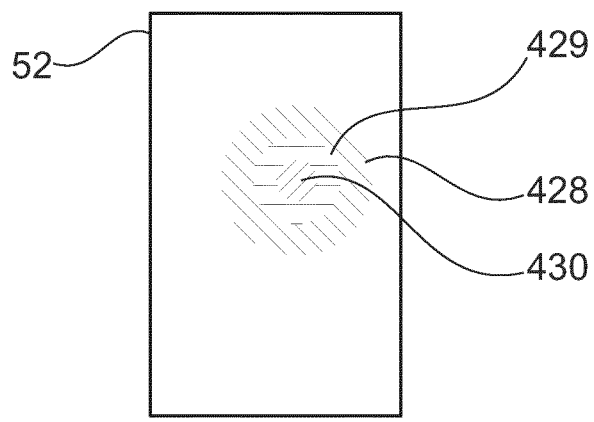
FIG. 11 shows a schematic drawing of a filtered scatter fraction of FIG. 10.

In step 108 the scatter fraction is filtered by a low pass filter having a large kernel, i.e. at least 1 cm. An example of the filtered scatter fraction is shown in FIG. 11.

Step 114 provides a linearized version of the pattern corrected X-ray image.

Figure 12:
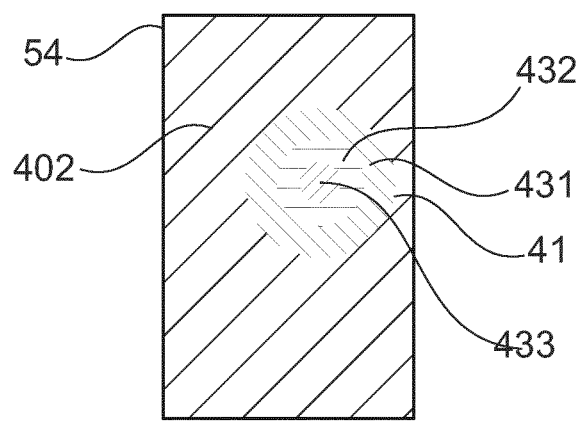
FIG. 12 shows a schematic drawing of a scatter signal being derived from the filtered scatter fraction of FIG. 11.

Step 109 the scatter signal is derived from the filtered scatter fraction by multiplying the filtered scatter fraction to the linearized version of the pattern corrected X-ray image. An example of the scatter signal is shown in FIG. 12.

In step 110, a factor smaller than 1 may be multiplied to the scatter signal. This leaves some scatter in the resulting corrected image. This may be performed to provide a resulting corrected image which is similar in appearance to the common X-ray images usually show some scatter. Therefore, only a fraction of the scatter signal is used to remove the scatter from the pattern corrected X-ray image. Step 110 is optional. Further functions may be used to determine a fraction of the scatter signal, e.g. SF'=SF-beta*SF^2 with beta in the range of 0.1 to 0.5, preferably 0.3, and SF being the scatter fraction.

In step 111 a corrected primary signal is determined from the scatter signal of step 110 and the linearized version of the pattern corrected X-ray image from step 114.

Figure 13:
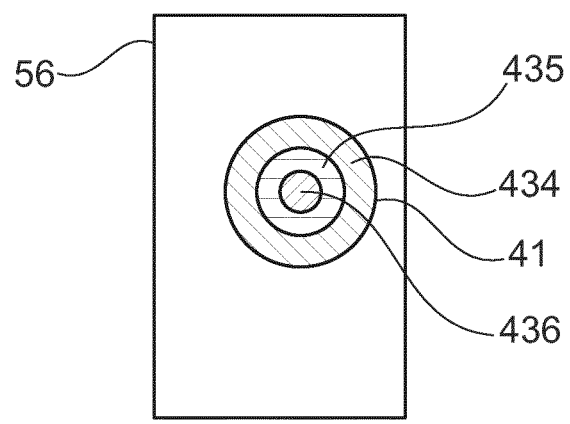
FIG. 13 shows a schematic drawing of a scatter corrected X-ray image determined by the scatter signal of FIG. 12.

In step 112 the logarithm of the corrected primary signal is determined resulting in a scatter corrected X-ray image. An example of a scatter corrected X-ray image is shown in FIG. 13.

In step 113 the scatter corrected X-ray image may be provided to an operator by a display.

Figure 2:
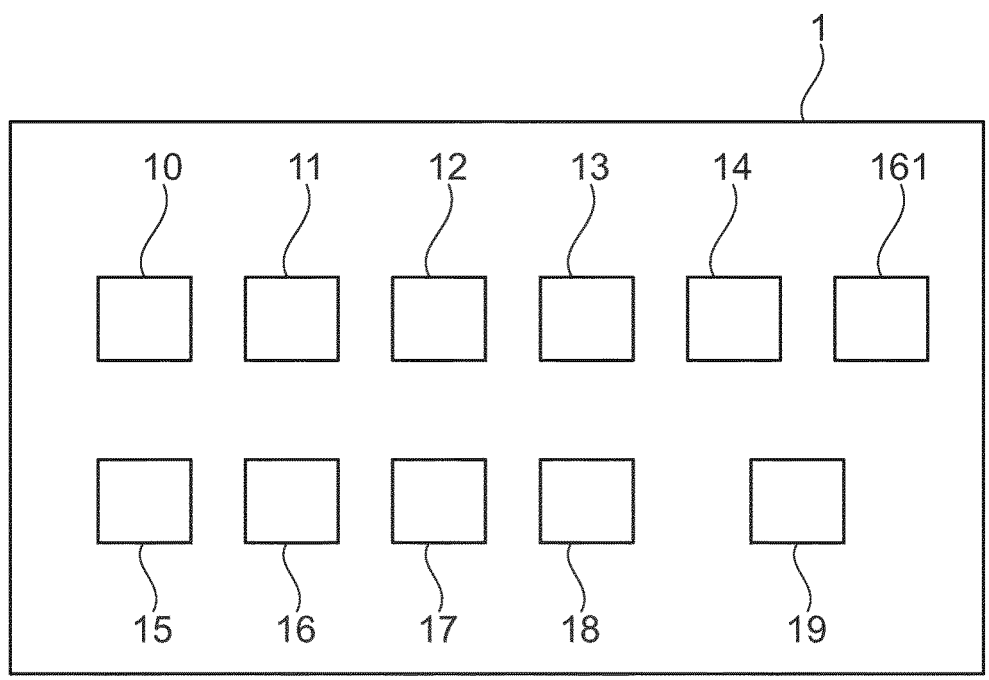
FIG. 2 shows a schematic drawing of a device for scatter correction in an X-ray image, the X-ray image having a superimposed structured pattern.

FIG. 2 shows a device 1 for scatter correction in an X-ray image, wherein the X-ray image has a superimposed structured pattern. The device comprises an X-ray receiving element 10, a pattern remover 11, a first subtraction module 12, a contrast measurement unit 13, a filter element 14, an estimation unit 15, a determination module 16, a linearization module 161, a second subtraction module 17, an output unit 18, and a processing unit 19.

The X-ray receiving element 10 may be an interface which may receive image data from an X-ray acquisition device. This means, that the X-ray receiving element 10 may receive the image data from a data storage or directly from an X-ray acquisition device. The X-ray receiving element 10 may receive raw data generated by the X-ray acquisition device or pre-processed data, wherein the pre-processed data is the processed raw data. Furthermore, the X-ray receiving element 10 may receive image data comprising a superimposed structured pattern. The superimposed structure pattern 31 may be an effect of a structure pattern element in the X-ray image acquisition device or a scatter reducing element in the X-ray image acquisition device. The provided X-ray image 30, 40 does not need to comprise any object data. It may be a flat X-ray image 30 or an X-ray image 40 comprising object data.

The pattern remover 11 processes of the X-ray image 30, 40 being received from the X-ray receiving element 10. The pattern remover 11 removes a superimposed structure pattern 31 from the X-ray image 30, 40 having a superimposed structured pattern 31. The pattern remover 11 provides a pattern corrected X-ray image 33, 43.

The first subtraction module 12 subtracts the pattern corrected X-ray image 33, 43 from the X-ray image 40 and provides a structured pattern image 32, 42. The structured pattern image 32, 42 comprises the structured pattern 31 being removed from the X-ray image 30, 40. Further, the structured pattern image 32, 42 comprises scatter data which has not been removed by the pattern remover 11. Scatter data may result from objects to be imaged or from scatter reducing elements of the X-ray image acquisition device.

The contrast measurement unit 13 applies a local structure contrast measurement function to the structured pattern image 32, 42. The local structure contrast measurement function may be an absolute value function, a minimum function, a maximum function, a standard deviation function, an average function, a median function, or a local FFT function for the amplitude etc. In this exemplary embodiment, the local structure contrast measurement function may be an absolute value function. The local structure contrast measurement function that provides the absolute values from the structured pattern image 32, 42 resulting in a structure contrast image 34, 44.

The filter element 14 is a low pass filter having a small kernel. The filter element 14 filters the structure contrast image 34, 44. This means, that high frequent changes of the contrast are filtered and only low frequent contrast changes remain in the image. This means, that the image data is smoothed. The result is a filtered structure contrast image 36, 46.

The estimation unit 15 estimates a primary fraction 48 of the X-ray image 40 based on the filtered structure contrast image 36, 46. The estimation of the primary fraction may be performed with a first filtered structure contrast image 46 comprising an object and a second filtered structure contrast image 36 being a reference image comprising no object.

The determination module 16 provides a filtered scatter signal 54 based on the primary fraction 48. Starting from the primary fraction 48 the scatter fraction 50 may be derived from the difference between the total signal of the pattern corrected image and the primary fraction 48. In exemplary first embodiment, the scatter fraction 50 is filtered with a low pass filter having a large kernel then the scatter signal 52 is derived from the scatter fraction 50 and the linearized pattern corrected X-ray image, wherein the linearized pattern corrected X-ray image may be provided by the linearization module 161. In an exemplary second embodiment, the scatter fraction 50 is multiplied with the linearized pattern corrected X-ray image resulting in a scatter signal 52. Then the scatter signal 52 is filtered with a low pass filter having a large kernel.

The second subtraction module 17 subtracts at least a fraction of the filtered scatter signal 54 from the pattern corrected X-ray image 43. The result is a scatter corrected X-ray image 56. The scatter corrected X-ray image 56 has more contrast than the pattern corrected X-ray image 43 since the processing of the scatter data in the scatter fraction or the scatter signal enhances the contrast of the scatter in the scatter fraction and scatter signal without adding any noise of the filtered scatter signal. Therefore, the subtraction of the filtered scatter signal from the pattern corrected X-ray image 43 removes the scatter very efficiently.

The output unit 18 may output the scatter corrected X-ray image 56. The output unit 18 may be a display or an interface which provides the data of the scatter corrected X-ray image 56.

The processing unit 19 may control the X-ray receiving element 10, the pattern remover 11, the first subtraction module 12, the contrast measurement unit 13, the filter element 14, the estimation unit 15, the determination module 16, the second subtraction module 17, and the output unit 18.

Figure 3A:
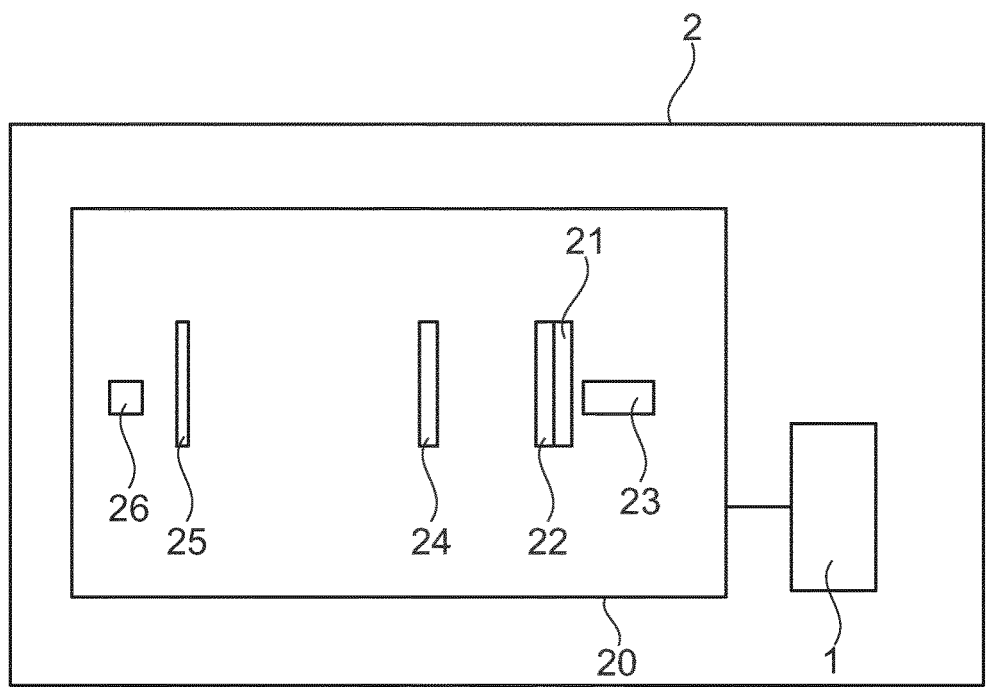
FIG. 3a, b show schematic drawings of different embodiments of a system for scatter correction in an X-ray image, the X-ray image having a superimposed structured pattern.

FIG. 3a shows a system 2 for scatter correction in an X-ray image having a superimposed structured pattern. The system comprises an X-ray image acquisition device 20 and a device 1 according to the above description. The X-ray image acquisition device 20 comprises an X-ray radiation source 26 and an X-ray detector 23. The X-ray radiation being emitted by the X-ray radiation source 26 propagates through a G0 grating 25. Then the X-ray radiation propagates further through a G1 grating 24 and then through a G2 grating 22. In this embodiment of the G2 grating 22 may comprise a structure pattern element 21. The structure pattern element 21 superimposes a structure pattern in the image being detected by the X-ray detector 23. The image data being detected by the X-ray detector 23 is provided to the device 1.

Figure 3B:
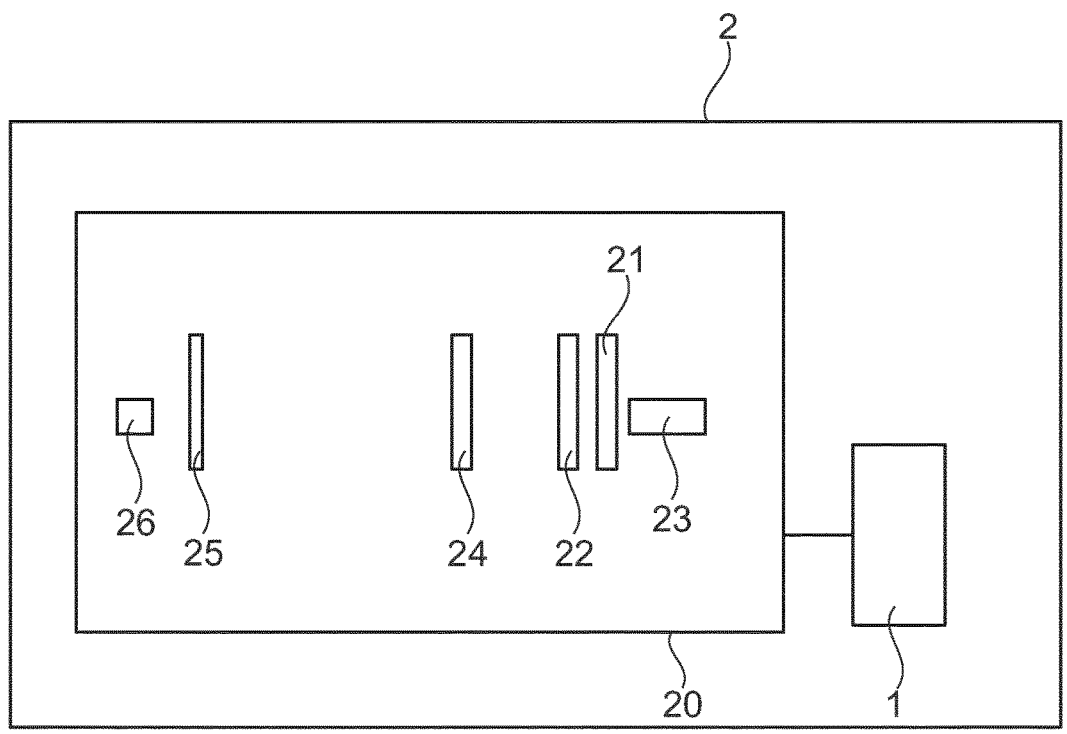

In another embodiment, according to FIG. 3b, the structure pattern element 21 is separate from the G2 grating 22. The structure pattern element 21 is located between the G2 grating 22 and the X-ray detector 23.

In a further embodiment (not shown), the system may comprise oscillating grids. The parameters of a software grid model are tuned using measurements according to the present invention. A large number of raw data may be stored. In an offline evaluation, the so-called kernel-parameters of a scatter model will be tuned to match the results of the measured scatter in a better way. These improved parameters can be applied to images being acquired with a regular oscillating grid.

Figure 4A:
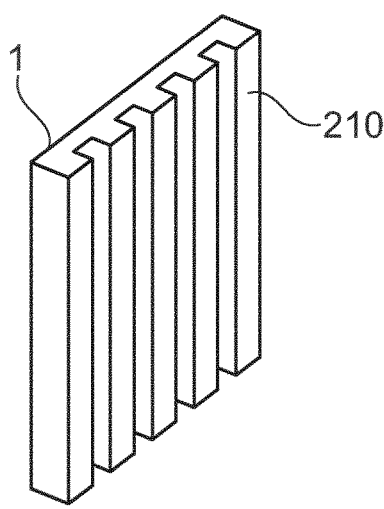
FIG. 4a-c show schematic drawing of different embodiments of a structure pattern element.

FIG. 4a shows the first exemplary embodiment of the structure pattern element 21. The structure pattern element 21 may be a plate having lamellas 210. The lamellas 210 has the same distance to each other. Further, the lamellas 210 have a width which is sufficient to provide a superimposed structured pattern on the acquired X-ray image.

Figure 4B:
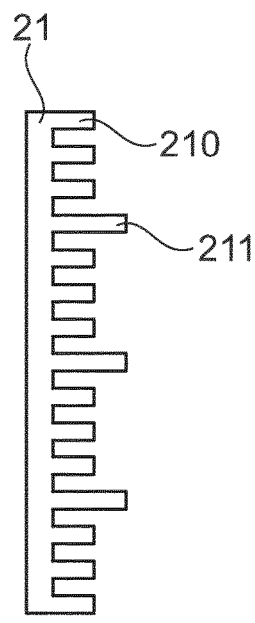

In another exemplary embodiment, according to FIG. 4b, the height of the lamellas 210 may be modulated. This means for example that every fourth lamella 211 may be higher than the rest of the lamellas 210. The distance between the fourth lamellas hundred 11 may be around 150 µm. The height increase of the lamellas 211 in relation to the lamellas 210 may be around 50 µm.

Figure 4C:
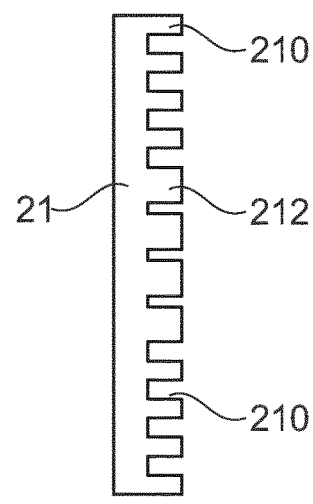

In a further exemplary embodiment, according to FIG. 4c, a duty cycle of the lamellas 210 may be modulated. This means that the structure pattern element 21 comprises regions having the lamellas printed 10 and having lamellas 212 which are wider than the lamellas 210. Furthermore, the free space between the lamellas 212 is smaller than the space between the lamellas 210. The region of the lamellas 210 and the region of the lamellas 212 may alternate such that the region of lamellas 212 follows each region of 210 and vice versa.

FIG. 5a shows a flat X-ray image 30 comprising a superimposed structured pattern 31 and flat scatter patterns 35. The flat X-ray image 30 does not comprise any object data and may be used as reference image. The flat X-ray image 30 may be parameterized using rotational symmetric functions CO. Parameters of this function CO may be the source image receptor distance (SID), the maximum value, the radius, and the center position. Using measurements, functions as: Radius having the SID, maximum voltage value as reference, or the center position having the angulation as parameter with angulation describing the tilt value of the X-ray beam, for example 40°, may be obtained. All these functions are independent of the very system, so the number of calibration images for CO may be limited to about one. The correction would use the function CO instead of the actual CO-image. Using the function CO a single flat X-ray image 30 may serve as reference for the processing of several X-ray images 40.

For example, the maximum grid contrast in a flat image may be measured. Thereby, the same voltage and filtration as in the X-ray image may be used. The result is a reference structure contrast value. The reference structure contrast value depends on the voltage. The higher the voltage the lower is the contrast. This allows to calibrate the voltage dependency and use a look up table for the conversion.

The grid contrast depends on the system Modulation Transfer Function MTF, which is constant with time. Using a two-dimensional image the two-dimensional maximum grid contrast measurement can take deviations of the grid contrast into account, that occur at the edges of the grid if the distance to the focal spot is not as specified for the grid.

In an example the two-dimensional maximum grid contrast measurement may be replaced by a constant value. This embodiment is applicable because the remaining scatter will not be correct totally, i.e. with a factor of 100%, but it will be implemented as a more moderate correction with a factor of less than 100%.

FIG. 5b shows an X-ray image 40 comprising an object 41 and superimposed structured pattern 31. Further the X-ray image 40 comprises scatter patterns 401. The object 41 comprises several regions 410, 411 and 412 having different contrast. The regions 410, 411 and 412 also comprise portions of the scatter patterns 401.

FIG. 5c shows a pattern corrected flat X-ray image 33 being derived by the flat X-ray image 30 of FIG. 5a. The pattern corrected flat X-ray image 33 may be processed by a pattern remover which may be a software algorithm removing the superimposed structured pattern in the flat X-ray image 30. The pattern corrected flat X-ray image 33 still comprises flat scatter patterns 35.

FIG. 5d shows a pattern corrected X-ray image 43 being derived from the X-ray image 40 comprising an object of FIG. 5b. The pattern corrected X-ray image 43 may be processed by a pattern remover which may be a software algorithm removing the superimposed structured pattern in the X-ray image 40. The pattern corrected X-ray image 33 still comprises scatter patterns 401. Further, the pattern corrected X-ray image 33 comprises object 41 with its regions 410, 411 and 412. The regions 410, 411 and 412 comprise portions of the scatter pattern 401.

FIG. 6a shows a flat structure pattern image 32 comprising the superimposed structured pattern 31 that has been removed by the pattern remover 11 from the flat X-ray image 30. The flat structure pattern image 32 is acquired by the first subtraction module 12 by subtracting the flat pattern corrected X-ray image 33 from the flat X-ray image 30. The flat structure pattern image 32 is a reference image.

FIG. 6b shows a structured pattern image 42 comprising the superimposed structured pattern 31 and some scatter data 413, 414, and 415 from the object 41 of the X-ray image 40. The scatter data 413, 414, and 415 are scatter data from the regions 410, 411, and 412 of the X-ray image 40, respectively. The structure pattern image 42 is acquired by the first subtraction module 12 by subtracting the pattern corrected X-ray image 43 from the X-ray image 40.

FIG. 7a shows a flat structure contrast image 34 being derived from the flat structure pattern image 32 by a local contrast measurement unit 13 with a local contrast measurement function. The mode of the structure pattern image 32 depends on the pattern removal algorithm of the pattern remover 11. Some removal algorithms provide a structure pattern image 32 which is zero in the average. Further removal algorithms provide a structure pattern image 32 which comprises the half maximum in the average. The local contrast measurement function is chosen depending on the removal algorithm. In the discussed example the removal algorithm provides a structure pattern image 32 which is zero in the average. The local contrast measurement function may thus be an absolute function which determines the absolute value of the structure pattern image 32.

The same applies to the structure contrast image 44 of FIG. 7b. The structure contrast image 44 is therefore acquired in the same way as the flat structure contrast image 34. The source of the structure contrast image 44 is the structured pattern image 42 which is processed by the local contrast measurement unit 13 in the way described above. The structure contrast image 44 comprises the superimposed structured pattern 31 as well as the contrast data 416, 417, and 418 from the regions 410, 411, and 412 of the X-ray image 40.

In FIG. 8a, a low pass filter having a small kernel is applied to the flat structure contrast image 34 of FIG. 7a by a filter element 14. The low pass filtering filters high frequencies situations in the flat structure contrast image 34. The result is a filtered flat structure contrast image 36. In the present example, the flat structure contrast image 34 comprises high frequent fluctuations in the corners of the image. Those fluctuations are filtered out in the flat structure contrast image 36 which becomes apparent in the blank corner regions of the flat structure contrast image 36.

FIG. 8b shows the filtered structure contrast image 46 being derived from filtering the structure contrast image 44 with low pass filter having a small kernel by the filter element 14. In the present example, the removal of the high frequent fluctuations in the image data may enhance the structures of the contrast data 416, 417, and 418 of the structure contrast image 44 which can be seen in the filtered contrast data 419, 420, and 421 of the filtered contrast structure image 46. Further, in the present example, the corner regions of the filtered structure contrast image 46 are blank which indicates that the structure contrast image 44 has high frequent fluctuations in the corner regions.

FIG. 9 shows the primary fraction 48 of the X-ray image 40. The primary fraction 48 is acquired by the division of the filtered structure contrast image 46 by the filtered flat structure contrast image 36. At the location of the object of the X-ray image 40 in the primary fraction 48, the primary fraction regions 422, 423, and 424 are shown in the primary fraction 48.

The primary fraction PF of the image may further be defined as: behind lead, there is no primary radiation and so there are no structured patterns visible and PF=0. In direct radiation without any object, the structured pattern visibility is at maximum. The peak-peak-contrast is only limited by the Modulation Transfer Function MTF of the system and is for example 25%. In a logarithmical image, this results in a constant peak-peak-difference independent of the exposure.

The primary fraction 48 may be used to determine the scatter fraction 50 as shown in FIG. 10. The scatter fraction 50 is so to say the negative of the primary fraction 48 since the addition of the primary fraction 48 with the scatter fraction 50 results in 1. The contrast of the primary fraction regions 422, 423, and 424 is inverted in the scatter fraction 50 which shows the scatter fraction regions 425, 426, and 427.

FIG. 11 shows the filtered scatter fraction 52 which results from filtering the scatter fraction 50 with a low pass filter having a large kernel. As shown in FIG. 11, the scatter fraction regions 425, 426, and want to 27 are smeared out to the filtered scatter fraction regions 428, 429, and 430. Due to the filtering, the contrast between the filtered scatter fraction regions 428, 429, and 430 is higher than the contrast between the scatter fraction regions 425, 426, and 427, whereas the noise in the filtered scatter fraction 52 is the same as in the scatter fraction 50.

FIG. 12 shows the scatter signal 54 being derived from the filtered scatter fraction 52. For determining the scatter signal 54, the filtered scatter fraction 52 is multiplied to the linearized pattern corrected X-ray image 43. The scatter signal 54 shows the object 41 with the filtered scattered regions 431, 432, and 433. Further, the scatter signal 54 comprises filtered scatter patterns 402.

The scatter corrected X-ray image 56 being shown in FIG. 13 is derived by subtracting the scatter signal 54 from the linearized pattern corrected X-ray image 43 and by applying the logarithm to the result. Due to the determination of the scatter signal 54 by filtering the scatter data, in this example the filtering of the scatter fraction 50, the scatter signal 54 comprises a high contrast. Therefore, by subtracting the high contrast scatter signal 54 from the linearized pattern corrected X-ray image 43, the contrast of the resulting image is also high. In a first embodiment, the total determined scatter signal 54 may be subtracted from the linearized pattern corrected X-ray image 43. This means, that all the scatter being determined by the scatter signal 54 is removed from the pattern corrected X-ray image 43. This may lead to the removal of all image data, i.e. image date equals zero, behind metal objects. Since the logarithm is applied to the subtracted image, zero values may cause errors. Therefore, according to a second embodiment only a fraction of the scatter signal 54 is subtracted from the linearized pattern corrected X-ray image 43. Therefore, some scatter remains in the resulting scatter corrected X-ray image 56 although most of the scatter is removed. This avoids zero values behind metal objects such that the logarithm of the image will show a properly corrected image. The preferred formula for providing a limits scatter correction SF' is SF'=SF−beta*SF^2 with beta in the range of 0.1 to 0.5, preferably 0.3, and SF being the scatter fraction 50. In another example, the scatter fraction 50 may be limited to a constant value if the scatter fraction 50 exceeds a threshold value. The constant value may be identical to the threshold value.

Figure 14:
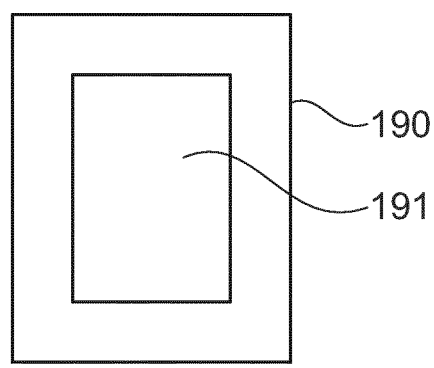
FIG. 14 shows a schematic drawing of a computer program element on a computer readable medium.

In another exemplary embodiment of the present invention according to FIG. 14, a computer program or a computer program element is provided that is characterized by being adapted to execute the method steps of the method 100 according to one of the preceding embodiments, on an appropriate system.

The computer program element 191 might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor 19. The data processor 19 may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element 191 might be able to provide all necessary steps to fulfil the procedure of an exemplary embodiment of the method as described above.

According to a further exemplary embodiment of the present invention, a computer readable medium 190, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should be noted that embodiments of the invention are described regarding different subject matters. In particular, some embodiments are described regarding method type claims whereas other embodiments are described regarding the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for scatter correction in an X-ray image, the device comprising:
   a memory that stores a plurality of instructions; and
   processor circuitry that couples to the memory and is configured to execute the instructions to:
   receive the X-ray image, the received X-ray image comprising a superimposed structured pattern and an object;
   remove the superimposed structured pattern from the X-ray image resulting in a pattern corrected X-ray image;
   subtract the pattern corrected X-ray image from the X-ray image resulting in a structured pattern image; and
   apply a local structure contrast measurement function to the structured pattern image resulting in a structure contrast image that includes contrast data of the object and that includes the superimposed structured pattern,
   wherein the scatter correction in the X ray image is partly based on the applying of the local contrast measurement function.

2. The device according to claim 1, wherein the processor circuitry is further configured to filter the structure contrast image to provide a filtered structure contrast image.

3. The device according to claim 2, wherein the processor circuitry is further configured to estimate a primary fraction of the X-ray image based on the filtered structure contrast image.

4. The device according to claim 3, wherein the processor circuitry is further configured to:

provide a filtered scatter signal based on a scatter fraction being determined from the primary fraction or a value derived from the scatter fraction; and subtract at least a fraction of the filtered scatter signal from the pattern corrected X-ray image resulting in a scatter corrected X-ray image.

5. The device according to claim 4, wherein the processor circuitry is configured to apply a filter on the scatter fraction or the value derived from the scatter fraction.

6. The device of claim 1, wherein the applying of the local contrast measurement function to the structured pattern image resulting in the structure contrast image includes applying, to the structured pattern image, at least one of an absolute value function, a minimum function, a maximum function, a standard deviation function, an average function, a median function, and a local Fast Fourier Transformation (FFT) function for an amplitude.

7. The device of claim 1, wherein in the structure contrast image, the superimposed structured pattern overlaps with the contrast data of the object.

8. A system for scatter correction in an X-ray image, the system comprising:
   an X-ray image acquisition device comprising a structure pattern element configured to provide the X-ray image with a superimposed structured pattern; and
   a device comprising:
      a memory that stores a plurality of instructions; and
      processor circuitry that couples to the memory and is configured to execute the instructions to:
         receive the X-ray image, the received X-ray image comprising the superimposed structured pattern and an object;
         remove the superimposed structured pattern from the X-ray image resulting in a pattern corrected X-ray image;
         subtract the pattern corrected X-ray image from the X-ray image resulting in a structured pattern image; and
         apply a local structure contrast measurement function to the structured pattern image resulting in a structure contrast image that includes contrast data of the object and that includes the superimposed structured pattern,
      wherein the scatter correction in the X ray image is partly based on the applying of the local contrast measurement function.

9. A method for scatter correction in an X-ray image, the method comprising:
   receiving the X-ray image, the received X-ray image having a superimposed structured pattern and an object;
   removing the superimposed structured pattern from the X-ray image resulting in a pattern corrected X-ray image;
   subtracting the pattern corrected X-ray image from the X-ray image resulting in a structured pattern image; and
   applying a local contrast measurement function to the structured pattern image resulting in a structure contrast image that includes contrast data of the object and that includes the superimposed structured pattern,
   wherein the scatter correction in the X ray image is partly based on the applying of the local contrast measurement function.

10. The method according to claim 9, further comprising estimating a primary fraction of the X-ray image based on the structure contrast image.

11. The method according to claim 10, further comprising:
   determining a filtered scatter signal from the primary fraction or a value derived from the primary fraction; and
   subtracting at least a fraction of the filtered scatter signal from the pattern corrected X-ray image resulting in a scatter corrected X-ray image.

12. The method according to claim 11, further comprising applying a filter on a scatter fraction or a value derived from the scatter fraction for providing the filtered scatter signal.

13. A non-transitory computer readable medium having one or more executable instructions stored thereon, which, when executed by a processor, cause the processor to perform a method for correcting scatter in an X-ray image, the method comprising:
   receiving the X-ray image, the received X-ray image having a superimposed structured pattern and an object;
   removing the superimposed structured pattern from the X-ray image resulting in a pattern corrected X-ray image;
   subtracting the pattern corrected X-ray image from the X-ray image resulting in a structured pattern image; and
   applying a local contrast measurement function to the structured pattern image resulting in a structure contrast image that includes contrast data of the object and that includes the superimposed structured pattern,
   wherein the scatter correction in the X ray image is partly based on the applying of the local contrast measurement function.

* * * * *